(12) United States Patent
Lodato et al.

(10) Patent No.: US 9,724,042 B1
(45) Date of Patent: Aug. 8, 2017

(54) DEVICE, SYSTEM, AND METHOD FOR ADJUSTING BIOMETRIC SENSING RATE BASED ON AVAILABLE ENERGY

(71) Applicant: VSN TECHNOLOGIES, INC., Fort Lauderdale, FL (US)

(72) Inventors: Franco Lodato, Weston, FL (US); Peter Aloumanis, Boca Raton, FL (US); Gustavo Leizerovich, Aventura, FL (US); Mansour Ghomeshi, Weston, FL (US); Biren Patel, Coral Springs, FL (US); Amit Verma, Sunrise, FL (US)

(73) Assignee: HOYOS VSN CORP., San Juan, PR (US)

( * ) Notice: Subject to any disclaimer, the term of this patent is extended or adjusted under 35 U.S.C. 154(b) by 0 days.

(21) Appl. No.: 15/216,939

(22) Filed: Jul. 22, 2016

Related U.S. Application Data (63) Continuation of application No. 14/574,576, filed on Dec. 18, 2014, now abandoned.

(51) Int. Cl.
| | |
|---|---|
| *A61B 5/0245* | (2006.01) |
| *A61B 5/00* | (2006.01) |
| *A61B 5/0205* | (2006.01) |
| *H02S 40/38* | (2014.01) |
| *H02S 50/00* | (2014.01) |
| *H02J 7/35* | (2006.01) |

(52) U.S. Cl.
CPC ........ *A61B 5/6831* (2013.01); *A61B 5/02055* (2013.01); *A61B 5/486* (2013.01); *A61B 5/6824* (2013.01); *A61B 5/6826* (2013.01); *A61B 5/6838* (2013.01); *A61B 5/7282* (2013.01); *A61B 5/743* (2013.01); *A61B 5/7445* (2013.01); *H02J 7/35* (2013.01); *H02S 40/38* (2014.12); *H02S 50/00* (2013.01); *A61B 2560/0209* (2013.01); *A61B 2560/0214* (2013.01)

(58) Field of Classification Search
None
See application file for complete search history.

(56) References Cited

U.S. PATENT DOCUMENTS

| | | | |
|---|---|---|---|
| 2003/0204140 A1* | 10/2003 | Ferek-Patric | A61N 1/36528 600/439 |
| 2008/0027502 A1* | 1/2008 | Ransom | A61B 5/036 607/42 |
| 2008/0036617 A1* | 2/2008 | Arms | B64C 27/006 340/679 |

(Continued)

*Primary Examiner* — Kennedy Schaetzle
(74) *Attorney, Agent, or Firm* — Patents on Demand P.A.; Brian K. Buchheit; Scott M. Garrett (57) ABSTRACT

A wearable health monitoring device includes one or more sensors for sampling biometric parameters of various physiological conditions of the wearer. The device is powered by a variable energy source that has an energy level that changes during operation. A rechargeable battery loses charge as it powers the device. A solar cell or cells can be used to recharge, or maintain charge of the rechargeable battery, or at least provide a supplemental power source to relieve the burden on the rechargeable battery to power the device. In some circumstances, the available energy can become diminished, and the device adjusts the rate at which it performs biometric measurements in order to conserve energy.

19 Claims, 8 Drawing Sheets

(56) References Cited

U.S. PATENT DOCUMENTS

| | | | |
|---|---|---|---|
| 2013/0190903 A1* | 7/2013 | Balakrishnan | A61B 5/7246 700/91 |
| 2013/0324855 A1* | 12/2013 | Lisogurski | A61B 5/0205 600/476 |
| 2014/0073486 A1* | 3/2014 | Ahmed | A61B 5/02405 482/9 |
| 2014/0214330 A1* | 7/2014 | Iyer | A61B 5/7203 702/19 |
| 2015/0220109 A1* | 8/2015 | von Badinski | G01P 15/00 340/539.12 |
| 2015/0265170 A1* | 9/2015 | Wisloff | A61B 5/02416 600/500 |
| 2015/0335947 A1* | 11/2015 | Kaushansky | A63B 24/0062 340/870.07 |
| 2016/0022201 A1* | 1/2016 | Arnold | A61B 5/1123 600/301 |
| 2016/0150978 A1* | 6/2016 | Yuen | A61B 5/0205 600/301 |

* cited by examiner

Embodiment 410

Embodiment 450

400

Sensors 420, 460
- Accelerometer
- Altimeter
- Skin Sensor
- Heart Rate Sensor
  ⋮

*FIG. 4*

Embodiment 510

Embodiment 530

DEVICE, SYSTEM, AND METHOD FOR ADJUSTING BIOMETRIC SENSING RATE BASED ON AVAILABLE ENERGY

CROSS REFERENCE

This application claims the benefit of prior U.S. patent application Ser. No. 14/574,576 filed Dec. 18, 2014, and titled "Enabling Comprehensive Heart Health Assessment Utilizing Biometrics From A Wearable Fitness Monitor," the entirety of which is hereby incorporated by reference.

BACKGROUND

Embodiments disclosed herein relate to the field of fitness and health monitors and, more particularly to reducing intra-device interference while taking biometric measurements.

As the public grows increasingly aware of health and healthy lifestyles, the desire for gadgets which aid in monitoring fitness grows in tandem. Fitness monitors such as pedometers, smart watches, and fitness bands have grown increasingly popular and often become necessary devices for maintaining healthy habits. These monitors can often track the number of steps, calories expended, heart rate, and goals a user wishes to achieve.

Taking an occasional biometric measurement at a fixed or otherwise immobile device may not always allow accurate diagnosis of a patient's condition as patterns in biometric parameters can be missed Accordingly, it is desirable for such devices to be mobile, and wearable, so that they can capture biometric measurements over a more significant period of time. To be mobile, however, a device must contain its own power source, which means a battery is used. A battery, however, add weight to the device, so it is common for a device that may be carried or worn for an extended period of time to be designed to use as small of a battery as possible. However, using a small battery reduces the operating time of the device.

Accordingly, there is a need in a wearable health monitoring device to conserve energy usage from a battery used to power the device.

BRIEF DESCRIPTION OF THE FIGURES

In the accompanying figures like reference numerals refer to identical or functionally similar elements throughout the separate views, together with the detailed description below, and are incorporated in and form part of the specification to further illustrate embodiments of concepts that include the claimed invention and explain various principles and advantages of those embodiments.

Those skilled in the field of the present disclosure will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. The details of well-known elements, structure, or processes that would be necessary to practice the embodiments, and that would be well known to those of skill in the art, are not necessarily shown and should be assumed to be present unless otherwise indicated.

DETAILED DESCRIPTION

Embodiments include devices and methods for sensing and monitoring biometric parameters of a wearer (person) powered at least in part by a variable energy source that provides a variable energy output. The device adjusts its operation in response to the power available from the variable energy source. Some embodiments, for example, include a wearable fitness monitoring device having at least one biometric sensor configured to sense a physiological condition of a wearer, and to produce a biometric parameter measurement of the physiological condition of the wearer. The device can further include a processor coupled to the one or more biometric sensors, where the processor is configured to process the biometric parameter measurement and control a sampling rate at which the biometric parameter measurement is sampled. The device is powered by a variable energy source contained in the device that provides a variable energy level. The power from the variable energy source is provided to the processor and the one or more biometric sensors, and the processor controls the sampling rate in proportion to the variable energy level of the variable energy source. When the variable energy level is low, the sampling rate is reduced so as to conserve power.

Figure 1:
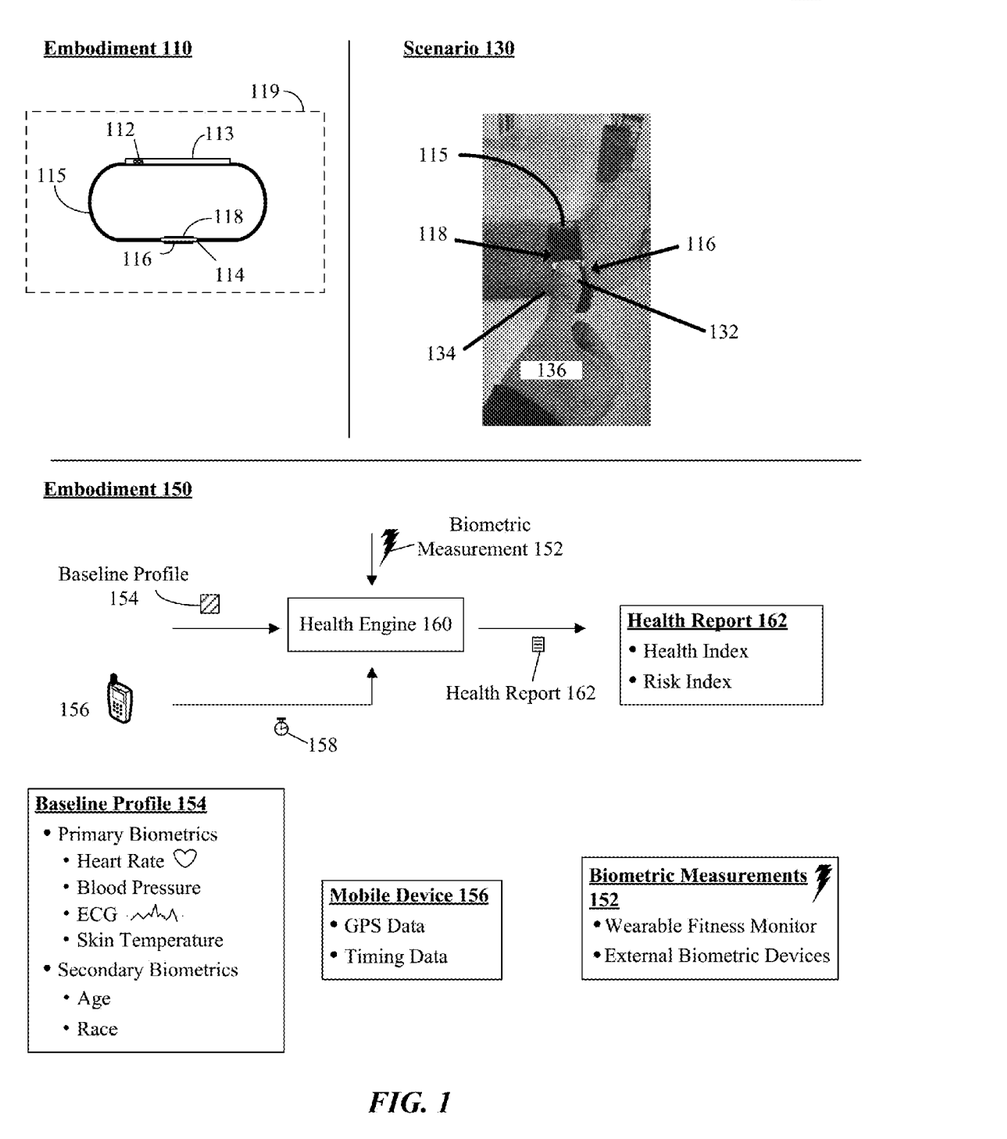
FIG. 1 is a schematic diagram illustrating a set of embodiments and a scenario for enabling comprehensive heart health assessment utilizing biometrics from a wearable fitness monitor in accordance with some embodiments.

FIG. 1 is a schematic diagram illustrating a set of embodiments 110, 150 and a scenario 130 for enabling comprehensive heart health assessment utilizing biometrics from a wearable fitness monitor in accordance with an embodiment of the inventive arrangements disclosed herein. Embodiments 110, 150 and/or scenario 130 can be present in the context of method 201, 251, system 300, embodiment 410, 450, 510, 530, 610, chart 700, and/or 800. Embodiment 110 and scenario 130 illustrate an organization and usage of a fitness monitor able to capture an electrocardiogram of a wearer via contacts 116, 118. Embodiment 150 illustrates a flow for generating a comprehensive assessment (e.g., health report 162) of the heart health of the wearer after electrocardiogram capture is completed.

As used herein, biometric measurements 152 can include, but is not limited to, primary biometrics, secondary biometrics, and the like. Primary biometrics can include, but is not limited to, heart rate, blood pressure, electrocardiogram, skin temperature, sleep patterns, calorie expenditure, weight, blood sugar level, respiration rate, oxygen saturation, and the like. Secondary biometrics can include, age, gender, family history, race, BMI, emotional state, and the like. It shall be appreciated that primary and/or secondary biometrics can be interchangeable.

In one instance, a baseline profile 154 can be generated for a wearer 136. In the instance, profile 154 can be manually and/or automatically generated. Profile 154 can include, but is not limited to, heart rate, blood pressure, respiration rate, age, race, gender, family history of disease, and the like. It shall be appreciated that profile 154 can be generated from aggregate biometric measurements or a single biometric measurement. It shall be appreciated that profile 154 can be generated using resting biometrics (e.g., resting pulse rate, resting skin temperature, etc).

In embodiment 110, a fitness monitor 119 can be a computing device configured to track one or more biometrics associated with a wearer. For example, monitor 119 can be a smart watch worn on the wrist which can track a wearer's heart rate. Fitness monitor 119 can include, but is not limited to, a band 115, a housing 113, an interactive button 112, a clasp 114, and the like. It shall be appreciated that housing 113 can include internal components such as sensors, circuitry, a display, and the like. In one instance, monitor 119 can be wearable computing device which can be worn on the wrist (or another part of the body, for example on the ear lobe, on the nose or other places) able to provide a wearer with a comprehensive heart health assessment via real-time or near-real time biometrics. In the instance, clasp 114 can include an interior contact 116 and an exterior contact 118 which can be utilized to obtain critical biometrics (e.g., primary biometrics—electrocardiogram) which can be evaluated to assess a wearer's health risk (e.g., heart attack risk, low blood pressure, etc). It shall be appreciated that fitness monitor 119 can include, smart watches, mobile phones, activity monitors, pedometers, heart rate monitors, and the like. Further, the fitness monitor 119 can include a sensor that is placed on one part of the wearer's body, such as on the user's ear lobe or nose). In yet another embodiment, the monitor 119 can include multiple pieces; one to sense the biometric information and another to display information related to the biometric information. With this latter embodiment, the sensor can be designed to be more discrete than would otherwise be if it were to be worn on the body.

In some embodiments, monitor 119 can periodically measure the heart rate of wearer 136 and can compare the measurements to acceptable heart rate ranges. In the embodiment, when measurements lie outside the ranges, an electrocardiogram can be executed by the monitor 119. In one configuration of the instance, the electrocardiogram can be communicated to a health care provider, the wearer, and the like.

In scenario 130, monitor 119 can be worn on a wrist of a wearer 136. In some embodiments, biometrics measurements (e.g., electrocardiogram, skin temperature) can be captured from wearer 136 when the wearer initiates contact with an interior contact 118 and an exterior contact 116 simultaneously. For example, user can press thumb 132 (e.g., or any other finger) against exterior contact 116 and wrist 124 can press against interior contact 118. It shall be understood that contact 116, 118 can be embedded within the band of monitor 119 permitting easy usage. In one instance, the contact 116, 118 can be distinct, indicating optimal thumb/wrist contact. In another instance, the contact 116, 118 can be indistinct (e.g., embedded within the length of the band) permitting a wearer to choose optimal contact points based on ergonomics. It shall be appreciated that biometric measurement collection can be trigged by any arbitrary mechanism.

It shall be appreciated that the monitor 119 can support health care provider directed evaluation. For example, a doctor (or trusted party) can trigger the monitor to conduct one or more tests. In one instance, the monitor 119 can be triggered manually and/or automatically. In the instance, automatic evaluation can be performed via an application communicatively linked to monitor 119. It shall be appreciated that the disclosure is not limited to an application linked directed evaluation, and can include any traditional and/or proprietary mechanism for triggering evaluation.

In some embodiments, the disclosure can support sharing the monitor between two or more users by utilizing biometric based identification to determine wearer identity. In the embodiment, collected data can be analyzed to determine the user identity and perform one or more automated and/or manual programmatic actions. For example, if the monitor detects that the person wearing the fitness monitor is different from a previous wearer, a second set of data can be maintained (and later combined if user chooses) or the collected data can be destroyed after an evaluation is performed (e.g., temporary evaluation). In embodiment 150, a biometric measurement 152 can be received by health engine 160. For example, when user 136 triggers biometric measurement capture 152, monitor 119 can automatically convey measurements to a mobile phone of the wearer for evaluation. In one instance, engine 160 can evaluate biometric measurement 152 utilizing a baseline profile 154. Baseline 152 can include, but is not limited to, primary biometrics (e.g., heart rate, Electrocardiogram, etc), secondary biometrics (e.g., age, race, etc), and the like. In the instance, engine 160 can evaluate biometric measurements 152 against baseline 154 to determine changes in health risk and/or health improvements. In some embodiments, engine 160 can generate a health report 162 which can include a numeric score indicating a wearer's health (e.g., health index) and risks (e.g., risk index). In some embodiments, monitor 119 can be utilized to determine heart health conditions (e.g., arrhythmia) in real-time or near real-time. In the embodiment, monitor 119 can trigger an emergency action which can assist in avoiding oncoming heart health conditions. That is, for example, by measuring the resting heart rate, blood pressure, skin temperature and evaluating the gender, family history for heart disease, weight, and ethnicity of the wearer, monitor 119 can determine heart functionality and assess heart failure risks. In one instance, monitor 119 can detect precursors of heart failure and present a warning notification for preventing a heart attack. For example, when the heart rate of a wearer is too high, monitor 119 can vibrate to indicate the wearer should take preventative measures.

In one configuration of the instance, mobile device 156 data can be utilized to enhance biometric evaluation. In the configuration, global positioning data and/or timing data from device 156 can be utilized to determine context (e.g., where, when) biometric collection occur. For example, when biometric measurements 152 are captured at a gym, appropriate thresholds for exercise can be utilized during biometric collection.

It shall be appreciated that biometric measurements 152 can be obtained from fitness monitor 119 and/or external biometric devices. It shall be appreciated that monitor 119 can perform traditional and/or proprietary tracking including, but not limited to, activity tracking (e.g., movement, duration, type), inactivity tracking, goals, and the like. It shall be appreciated that the disclosure can be configured to conform to a wrist strap enabling the disclosure to be fitted to any fitness monitor, smart watch, watch, wearable device, and the like.

It shall be appreciated that the monitor 119 can utilized traditional and/or proprietary mechanisms to heuristically learn customized and/or novel behaviors. In one instance, historic actions and/or behaviors of a user can be analyzed to determine an appropriate programmatic action to be performed responsive to a data collection initiation, an evaluation completion, a health emergency condition, and the like. The heuristic learning may leverage a hidden Markov model (HMM) In some embodiments. In some embodiments, a Bayesian network or model can be used as a probabilistic graphical model to represent variables and their dependencies through a directed acyclic graph (DAG) to implement heuristic functionality detailed herein. In one contemplated implementation topic maps (or other semantic technology such as a resource description framework (RDF) based model) can be utilized when storing knowledge and knowledge based relationships to permit reactive heuristics to be applied per the disclosure. One of ordinary skill realizes that other heuristic techniques besides those detailed herein can be implemented for the heuristic learning and for dynamic statistically based actions driven by the biometric data collected by a device.

Figure 2:
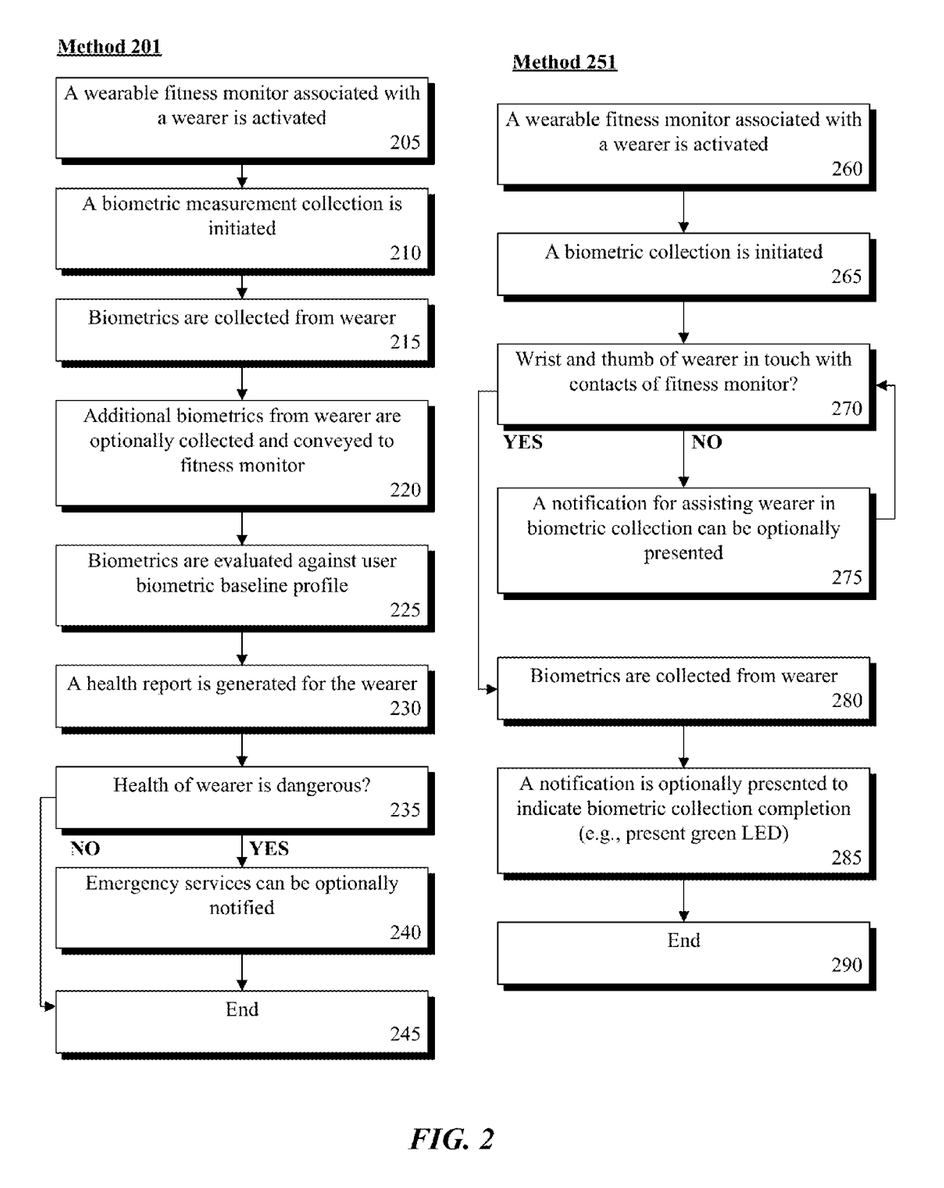
FIG. 2 is a flowchart illustrating a set of methods for enabling comprehensive heart health assessment utilizing biometrics from a wearable fitness monitor in accordance with some embodiments.

FIG. 2 is a flowchart illustrating a set of methods 201, 251 for enabling comprehensive heart health assessment utilizing biometrics from a wearable fitness monitor in accordance with an embodiment of the inventive arrangements disclosed herein. Method 201, 251 can be present in the context of embodiments 110, 150, scenario 130, system 300, embodiments 410, 450, 510, 530, 610, chart 700, and/or 800.

Method 201 illustrates a series of steps for generating a health report obtained from biometrics of a wearer of a fitness monitor. In step 205, a wearable fitness monitor associated with a wearer is activated. Activation can be manually and/or automatically performed. In step 210, a biometric measurement collection is initiated. The initiation can be manually and/or automatically triggered. For example, the collection can be automatically triggered twice a day, once in the morning and once in the evening. In step 215, biometrics can be collected from the wearer interacting with the fitness monitor. In step 220, additional biometrics from the wearer can be optionally collected and conveyed to the fitness monitor. For example, biometric measurements from a blood glucose monitoring device can be captured and conveyed to the fitness monitor. In step 225, biometrics can be evaluated against a user biometric baseline profile. In step 230, a health report can be generated for the wearer. The report can be generated in real-time or near real-time. In step 235, if the health of the wearer is dangerous, the method can continue to step 240, else proceed to step 245. In step 240, emergency services can be optionally notified. In some embodiments, an emergency drone with emergency medical supplies and/or equipment can be dispatched to the wearer's location. In step 245, the method can end.

Method 251 illustrates a series of steps for capturing biometrics from a wearable fitness monitor. In step 260, a wearable fitness monitor associated with a wearer can be activated. In step 265, a biometric collection can be initiated. In step 270, if the wrist and the thumb of the wearer is in touch with the contacts of the fitness monitor, the method can continue to step 280, else proceed to step 275. It shall be appreciated that biometric collection can be initiated from an application (e.g., mobile phone application) linked to the fitness monitor. In step 275, a notification for assisting the wearer can be optionally presented. In step 280, biometrics can be collected from the wearer. In step 285, a notification can be optionally presented to indicate biometrics collection completed. For example, when biometrics are completed, an LED on the fitness monitor can be triggered to present a green color. In step 290, the method can end. It shall be appreciated that method 201, 251 can be performed in real-time or near real-time. Further, method 201, 251 can be performed in serial and/or in parallel.

Figure 3:
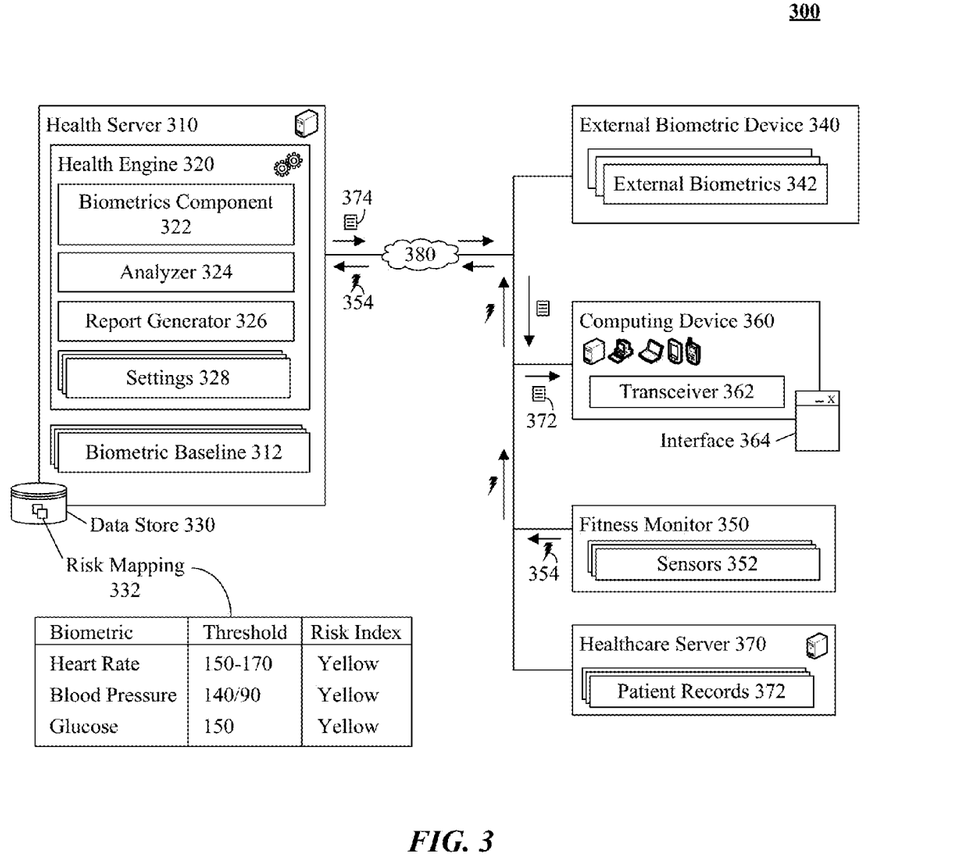
FIG. 3 is a schematic diagram illustrating a system for enabling comprehensive heart health assessment utilizing biometrics from a wearable fitness monitor in accordance with some embodiments.

FIG. 3 is a schematic diagram illustrating a system 300 for enabling comprehensive heart health assessment utilizing biometrics from a wearable fitness monitor in accordance with an embodiment of the inventive arrangements disclosed herein. System 300 can be present in the context of embodiments 110, 150, scenario 130, method 201, 251, embodiment 410, 450, 510, 530, 610, chart 700, and/or 800. In system 300, engine 320 can permit a comprehensive heart health assessment to be performed utilizing risk mapping 332. System 300 components can be communicatively linked via one or more networks 380.

Health server 310 can be a hardware/software entity for executing engine 320. Server 310 can include, but is not limited to, engine 320, data store 330, and the like. Server 310 functionality can include, but is not limited to, file sharing, notification handling, encryption, and the like. In one instance, server 310 can be a component of a cloud based fitness service able to provide real-time or near real-time fitness assessment of a wearer using wearable fitness monitor 350.

Health engine 320 can be a hardware/software element for enabling heart fitness assessment and/or management of heart health problems. Engine 320 can include, but is not limited to, biometrics component 322, analyzer 324, report generator 326, settings 328, and the like. Engine 320 functionality can include, but is not limited to, communication handling, monitor 350 registration, software management (e.g., monitor 350 firmware), and the like. In some embodiments, engine 320 can facilitate biometric identification using a unique data points derived from a user biometric baseline 312 (e.g., personal health patterns). In the embodiment, the data points can be utilized to link a user identity with a computer system user identity or unique information as a method for personal security or payment transactions combined with other existing ID systems. In one instance, the engine 320 can trigger random biometric collection to foster user conformity to healthy lifestyle habits. The random collection can be a statistically relevant sampling of the biometrics suitable for a specific purpose. The random collection may, but need not, be truly random and pseudo-random or even non-random but time spaced collections can be used in various contemplated embodiment's.

Biometrics component 322 can be a hardware/software entity for capturing biometric measurement 354. Component 322 functionality can include measurement 354 validation, baseline 312 generation, risk mapping 332 creation, and the like. In one instance, component 322 can utilize patient records 372 to generate an appropriate baseline 312 for a wearer of monitor 350. In some embodiments, component 322 can capture external biometrics 342 from external biometric device 340.

Analyzer 324 can be a hardware/software element for analyzing primary and/or secondary biometrics. Analyzer 324 functionality can include, but is not limited to, threshold evaluation, primary biometric analysis, secondary biometric analysis, feedback collection, and the like. In some embodiments, analyzer 324 can utilize one or more algorithms which combine primary and secondary measurements to generate feedback (e.g., assessment 374) for the wearer. In the embodiment, feedback can include audible, visual, and/or tactile feedback through monitor 350 and/or device 360.

Report generator 326 can be a hardware/software entity for generating an assessment 374. Generator 326 functionality can include, but is not limited to, assessment 374 generation, notification generation, health report creation, and the like. In some embodiments, generator 326 can be utilized to generate a health index, a risk index, and the like.

Settings 328 can be one or more options for configuring the behavior of system 300, server 310, and/or engine 320. Settings 328 can include, but is not limited to, biometrics component 322 options, analyzer 324 settings, report generator 326 options, biometric baseline 312 settings, and the like. Settings 328 can be persisted within data store 330, computing device 360, monitor 350, and the like. Settings 328 can be manually and/or automatically established. In one instance, settings 328 can be heuristically established.

Biometric baseline 312 can be a data set which can include primary and/or secondary biometrics. Baseline 312 can conform to one or more traditional and/or proprietary formats. Formats can include, but are not limited to, text format, Extensible Markup Language, binary encoded format, and the like. In some embodiments, baseline 312 can be persisted in patient records 372. It shall be appreciated that baseline 312 can include compression, encryption, and the like.

Data store 330 can be a hardware/software component able to persist settings 328, baseline 312, mapping 332, and the like. Data store 330 can be a Storage Area Network (SAN), Network Attached Storage (NAS), and the like. Data store 330 can conform to a relational database management system (RDBMS), object oriented database management system (OODBMS), and the like. Data store 330 can be communicatively linked to server 310 in one or more traditional and/or proprietary mechanisms. In one instance, data store 330 can be a component of Structured Query Language (SQL) complaint database.

Risk mapping 332 can be a data set for evaluating biometric measurements 354. Mapping 332 can include a biometric type, a threshold value, and the like. For example, mapping 332 can include threshold values for resting glucose (e.g., 150) and heart rate (e.g., 150-170) which can be utilized to determine a risk index. That is, when measurements 354 meet threshold values a risk index of yellow can be determined. It shall be appreciated risk index can include alphanumeric values, fuzzy logic values, and the like. It shall be understood that thresholds can be linked to permit complex health states to be evaluated. That is, thresholds can be evaluated in tandem and not in isolation. For example, when two biometric measurements (e.g., heart rate, skin temperature) exceed the threshold values, then a red level index can be generated (e.g., indicating an emergency). In one instance, mapping 332 can be manually and/or automatically generated based on secondary and/or primary biometrics.

External biometric device 340 can be a hardware/software entity for obtaining external biometrics 342. Device 340 can include, but is not limited to, a home health monitor (e.g., blood pressure kit), a commercial monitoring device, and the like. Device 340 can include, but is not limited to, a transceiver, a display, a biometric monitoring component, and the like.

Fitness monitor 350 can be a hardware/software element for capturing biometric measurements 354 and/or presenting assessment 374. Monitor 350 can include one or more software applications (e.g., calorie tracker, goal tracker), sensors 352, and the like. It shall be appreciated that sensors 352 can be constructed from traditional and/or proprietary materials. It shall be understood that sensors 352 can be continuously active, intermittently active (e.g., for power conservation), and the like. It shall be appreciated that monitor 350 can include sensors which can measure skin temperature, ambient temperature, skin galvanic response, and the like. In some embodiments, the monitor 350 can generate an alert when biometrics measurements indicate that a hypoglycemic episode is likely to occur. It shall be appreciated that monitor 350 can be associated with traditional and/or proprietary communication technologies, including, but not limited to, near field communication (NFC), WiFi, and the like. In one instance, monitor 350 can utilize BLUETOOTH technology to communicate and/or receive transmissions.

Computing device 360 can be a hardware/software permitting the execution of engine 320 and/or engine 320 components. Device 360 can include, but is not limited to, input/output components, user settings, transceiver 362, interface 364, and the like. Computing device 360 can include, but is not limited to, a desktop computer, a laptop computer, a tablet computing device, a personal digital assistant (PDA), a mobile phone, and the like. Interface 364 can be a user interactive component permitting interaction and/or presentation of assessment 374. Interface 364 capabilities can include a graphical user interface (GUI), voice user interface (VUI), mixed-mode interface, and the like. In one instance, interface 364 can be communicatively linked to computing device 360.

Healthcare server 370 can be a hardware/software entity for persisting patient records 372. Server 370 can include, but is not limited to, patient records 372, Web-based applications, configuration settings, and the like. In one instance, server 370 can be communicatively linked to fitness monitor 350 enabling real-time or near real-time heart health monitoring. In the instance, server 370 can convey measurements 354 and/or assessment 374 to one or more health care providers (e.g., physicians).

Network 380 can be an electrical and/or computer network connecting one or more system 300 components. Network 380 can include, but is not limited to, twisted pair cabling, optical fiber, coaxial cable, and the like. Network 380 can include any combination of wired and/or wireless components. Network 380 topologies can include, but is not limited to, bus, star, mesh, and the like. Network 380 types can include, but are not limited to, Local Area Network (LAN), Wide Area Network (WAN), Virtual Private Network (VPN) and the like.

In some embodiments, the system 300 can conform to a Service Oriented Architecture. In one instance, engine 320 can permit the usage of multiple fitness monitors by a single wearer, multiple wearers, and the like. In some embodiments, engine 320 can be present within device 360 which can communicate with proximate monitor 350 to assist in self-treatment of a wearer.

Figure 4:
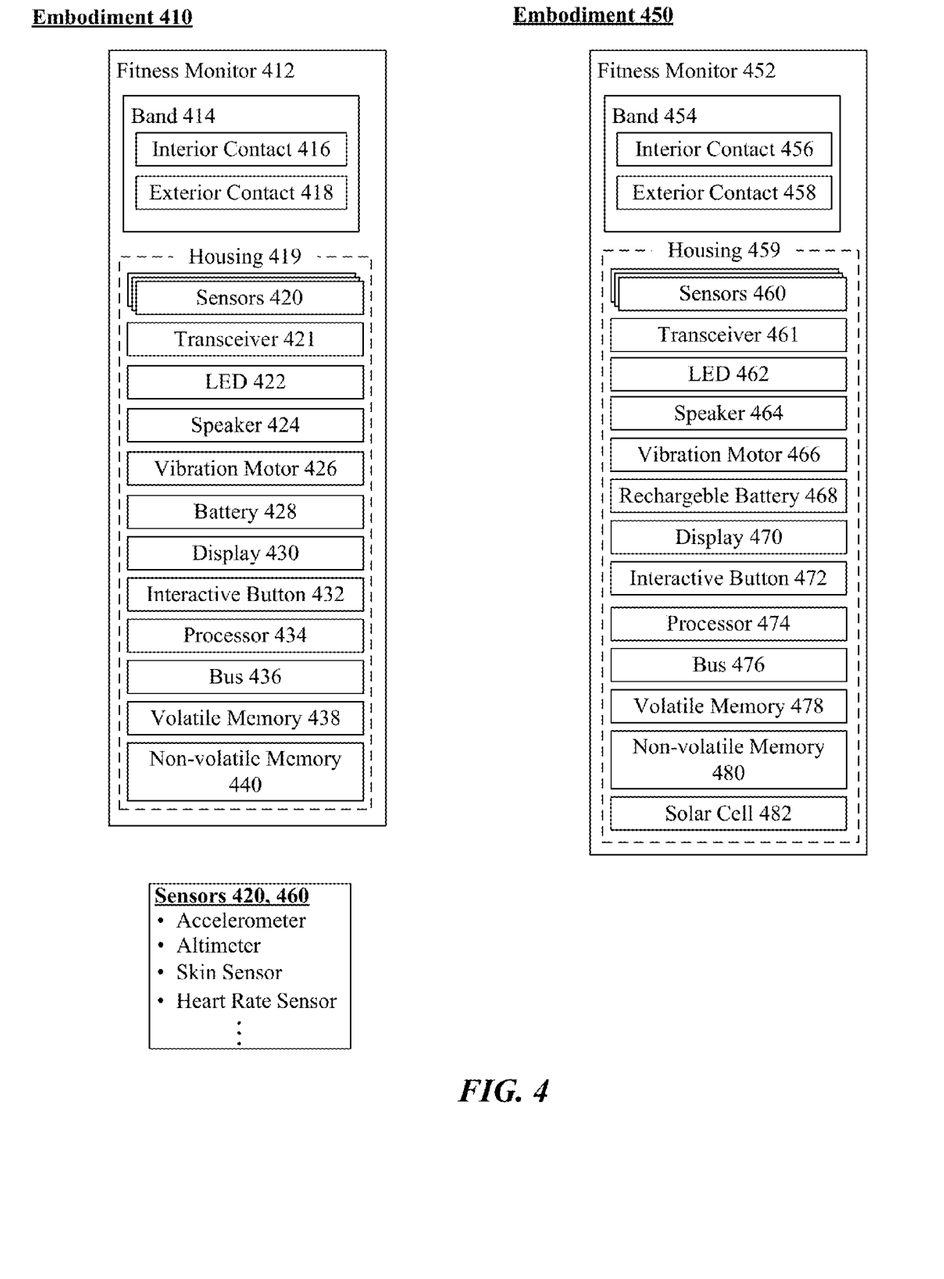
FIG. 4 is a schematic diagram illustrating an embodiment for enabling comprehensive heart health assessment utilizing biometrics from a wearable fitness monitor in accordance with some embodiments.

FIG. 4 is a schematic diagram illustrating an embodiment 410, 450 for enabling comprehensive heart health assessment utilizing biometrics from a wearable fitness monitor in accordance with an embodiment of the inventive arrangements disclosed herein. Embodiments 410, 450 can be present in the context of embodiments 110, 150, scenario 130, method 201, 251, system 300, embodiments 510, 530, 610, chart 700, and/or 800.

In embodiment 410, a fitness monitor 412 can include a band 414 and a housing 419. Band 414 can include, but is not limited to, an interior contact 416 and an exterior contact 418. Housing 419 can include sensors 420, transceiver 421, LED 422, loudspeaker 424 (e.g., piezoelectric speaker), vibration motor 426, battery 428, display 430, interactive button 432, process 434, bus 436, volatile memory 438, non-volatile memory 440, and the like. It shall be appreciated that monitor 412 can include additional elements or can lack elements presented herein. It shall be understood that components 416, 418, 420-440 can be present within band 414 and/or housing 419.

In one instance, monitor 412 can capture ambient temperature, relative humidity, skin temperature, and exposed time to heat to determine dehydration and/or heat stroke probability. In the instance, an alert (e.g., audible alert) can be generated when the measurements lie outside an acceptable range based on the baseline profile of the wearer.

In embodiment 450, a fitness monitor 452 can include a band 454 and a housing 459. Band 454 can include, but is not limited to, an interior contact 456, an exterior contact 458, and the like. Housing 459 can include, but is not limited to, sensors 460, transceiver 461, LED 462, loudspeaker 464, vibration motor 466, rechargeable battery 468, display 470, interactive button 472, processor 474, bus 476, volatile memory 478, non-volatile memory 480, solar cell 482, and the like. In one instance, monitor 412 can include one or more solar cells 482 which can utilize daylight to charge rechargeable battery 468. It shall be appreciated that monitor 412 can include additional elements or can lack elements presented herein. It shall be understood that components 456, 458, 460, 482 can be present within band 454 and/or housing 459. The solar cell and rechargeable battery are variable energy sources that provide a variable energy level. For example, as the intensity of light incident on the solar cells 482 increases or decreases, the power output of the solar cells 482 likewise increases or decreases. The rechargeable battery 468 loses or gains charge depending on whether it is being discharged or charged.

In some embodiments, the monitor 452 can adjust a rate at which biometric measurement are sampled based on the energy level of the variable energy source. If the available energy is decreasing, the sampling rate can be reduced, either in proportion or in steps based on one or more energy thresholds of available energy. The available energy can be determined, for example, by use of a battery fuel gauge which monitors the coulombic transfer of charge into and out of the rechargeable battery relative to its charge capacity. Likewise, the output of the solar cell can be determined, for example, based on a voltage output of the solar cells. The output voltage can be regulated to provide charge to the rechargeable battery or, if the output is insufficient to recharge the battery, then it can act as a supplemental power source to at least reduce the amount of energy being consumed from the rechargeable battery.

In some embodiments monitor 452 can suspend battery charging and other non-essential components of the monitor 452 during electrocardiogram measurements to reduce noise contamination. In another embodiment, components (e.g., sensors, speaker) can be adaptively adjusted based on the output of solar cells 482 and/or battery 468 charge level which can maximize battery life of the monitor 452. That is, sensor 460 measurement rates can be a function of solar cell 482 and/or battery 468 output.

It shall be appreciated that sensors 420, 460 can include, but is not limited to, an accelerometer, an altimeter, a skin sensor, a heart rate sensor, and the like. It shall be appreciated that the fitness monitor of the disclosure can utilize multiple similar components (e.g., dual processors, multiple buttons), and the like. In some embodiments, the fitness monitor can include a sensor processor (e.g., APPLE M7/M8 motion co-processor) which be utilized to capture sensor data in real-time or near real-time.

Figure 5:
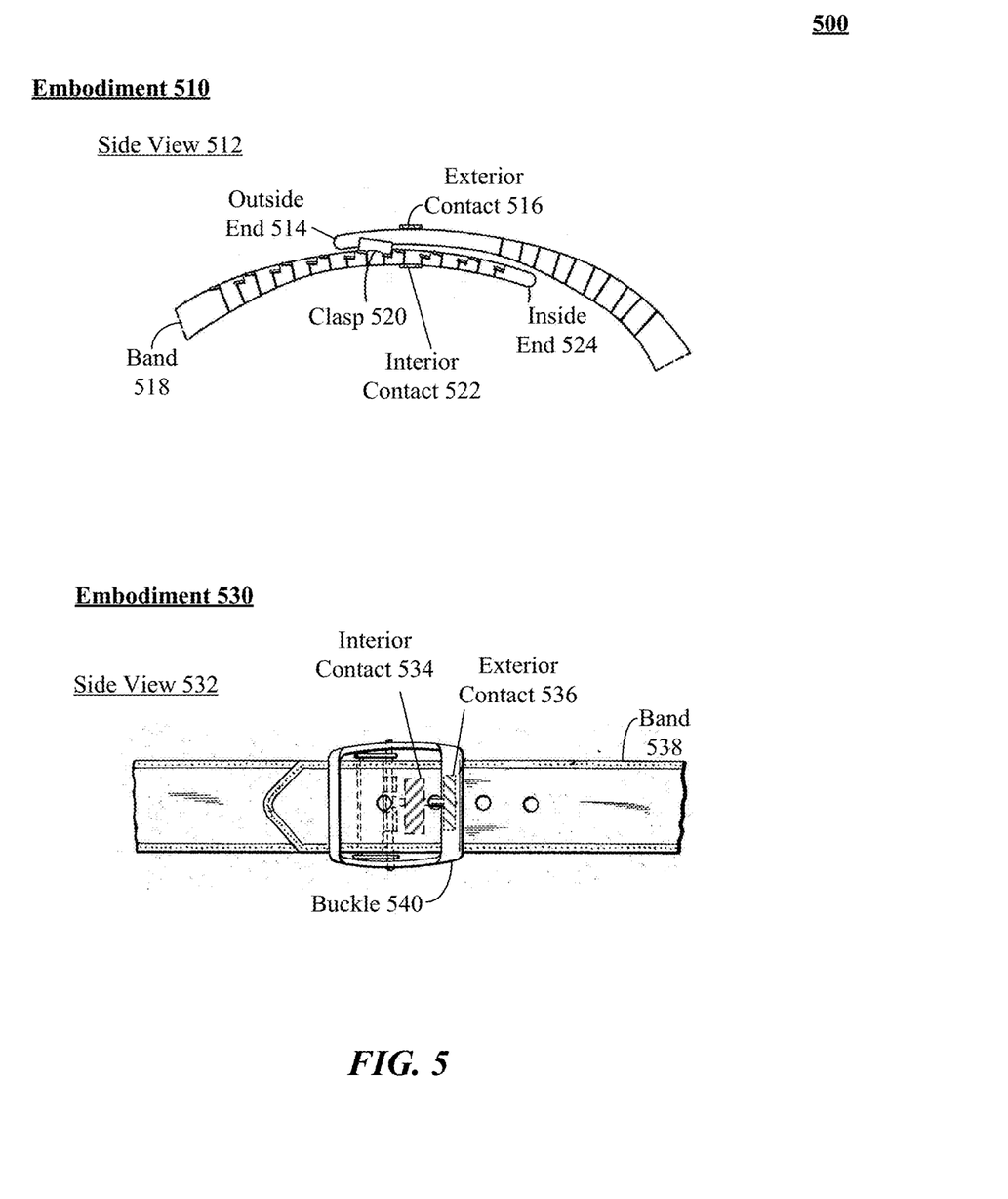
FIG. 5 is a schematic diagram illustrating a set of embodiments for enabling comprehensive heart health assessment utilizing biometrics from a wearable fitness monitor in accordance with some embodiments.

FIG. 5 is a schematic diagram illustrating a set of embodiments 510, 530 for enabling comprehensive heart health assessment utilizing biometrics from a wearable fitness monitor in accordance with an embodiment of the inventive arrangements disclosed herein. Embodiments 510, 530 can be present in the context of embodiments 110, 150, scenario 130, method 201, 251, system 300, embodiments 410, 450, 610, chart 700, and/or 800.

Embodiment 510 illustrates a side view 512 of a magnetically fastened band of a fitness monitor. In the embodiment, the outside end 514 of band can be fastened to the inside end 524 of band via a magnetic clasp 520. It shall be appreciated that the clasp can include other fastening mechanisms. In one configuration of the embodiment, an exterior contact 516 for a biometric sensor can be exposed to the outside of the band. In the configuration of the embodiment, an interior contact 522 for a biometric sensor can be exposed to the inside of the band. It shall be appreciated that the contact 516, 522 can be linked to the same biometric sensor, a different biometric sensor, and the like.

Embodiment 530 illustrates a side view 532 of a traditional buckle fastened band 538. In the embodiment, the buckle 540 can fasten two ends of the band which can position interior contact 534 and/or exterior contact 536 within the middle of the wrist (e.g., proximate to the pulse). In some embodiments, exterior contact 536 can be present within buckle 540. For example, a wearer can press the buckle 540 to initiate biometric measurement capture and assessment.

It shall be appreciated that contacts 516, 522, 534, 536 can include multiple contacts which can permit the usage of the contacts regardless of the location of the fastening of the band 518, 538. In one instance, each notch of the band can include a proximate sensor. In another instance, a sensor can be embedded within the length of the band.

Figure 6:
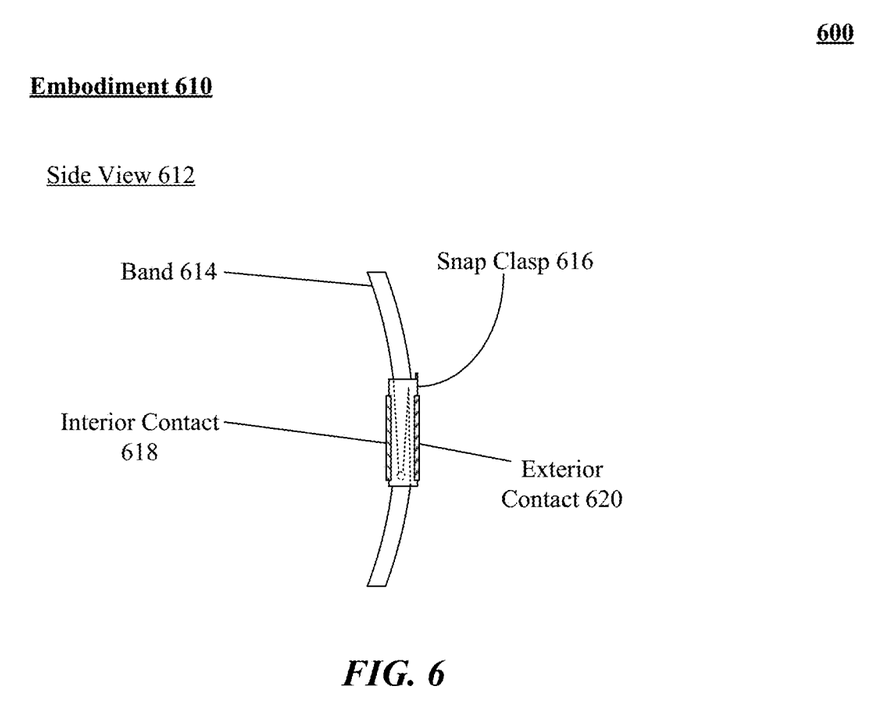
FIG. 6 is a schematic diagram illustrating an embodiment for enabling comprehensive heart health assessment utilizing biometrics from a wearable fitness monitor in accordance with some embodiments.

FIG. 6 is a schematic diagram illustrating an embodiment 610 for enabling comprehensive heart health assessment utilizing biometrics from a wearable fitness monitor in accordance with an embodiment of the inventive arrangements disclosed herein. Embodiments 610 can be present in the context of embodiments 110, 150, scenario 130, method 201, 251, system 300, embodiments 410, 450, 510, 530, chart 700, and/or 800.

Embodiment 610 illustrates a snap clasp 616 which can include an interior contact 618 and an exterior contact 620. In the embodiment, band 614 can be fastened with a snap clasp (e.g., friction fit) which can position contacts 618, 620 within optimum positions for obtaining biometrics on a wearer's wrist. In one instance, the entire interior portion of the clasp 616 can include contact 618 which can maximize contact with wrist of a wearer. In the instance, the entire exterior portion of the clasp can include contact 620 which can maximize contact with the thumb of a wearer.

Figure 7:
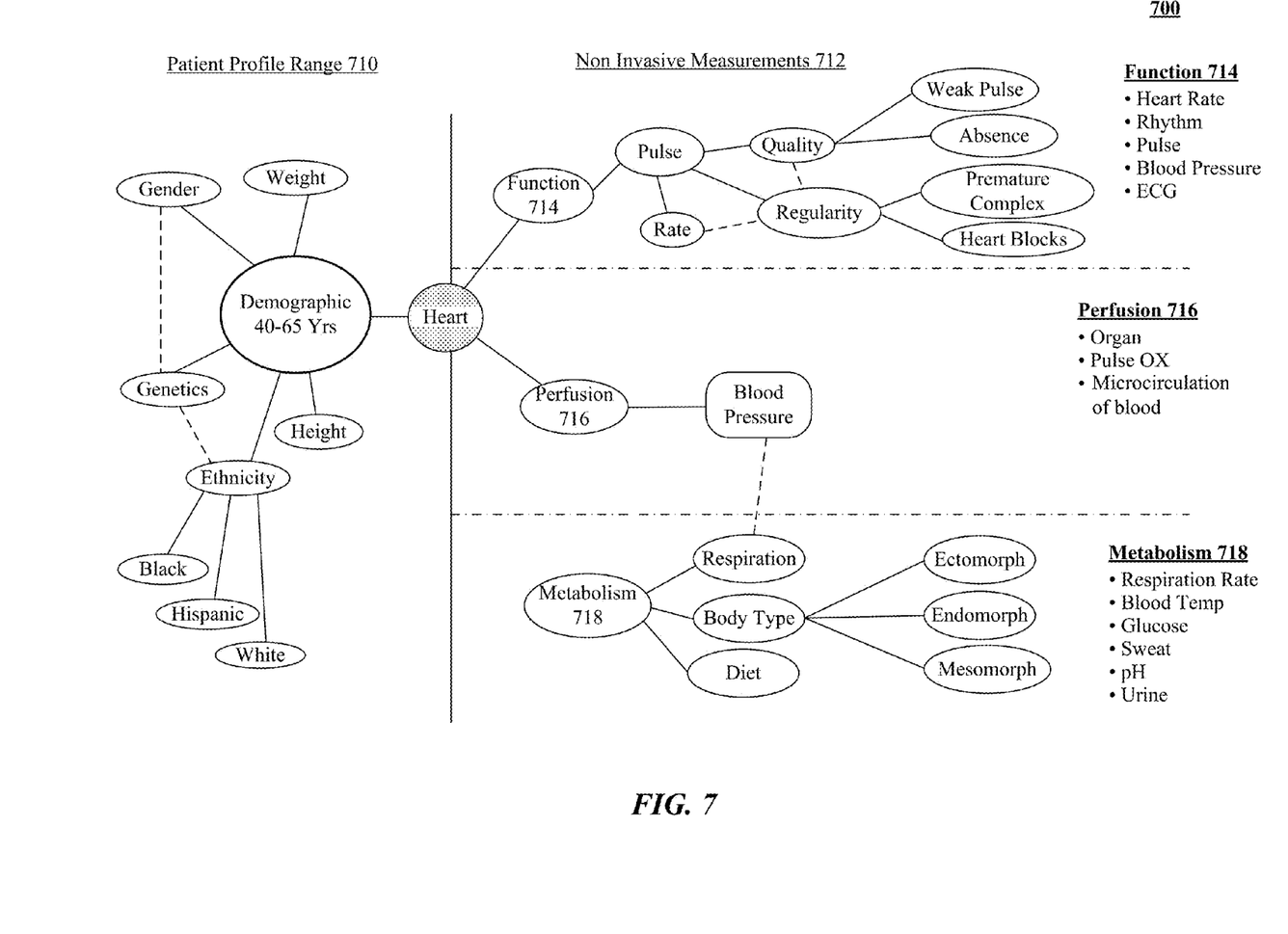
FIG. 7 is a schematic diagram illustrating a chart for enabling comprehensive heart health assessment utilizing biometrics from a wearable fitness monitor in accordance with some embodiments.

FIG. 7 is a schematic diagram illustrating a chart 700 for enabling comprehensive heart health assessment utilizing biometrics from a wearable fitness monitor in accordance with an embodiment of the inventive arrangements disclosed herein. Chart 700 can be present in the context of embodiments 110, 150, scenario 130, method 201, 251, system 300, embodiments 410, 450, 510, 530, embodiments 610, and/or chart 800.

Chart 700 illustrates a set of profile ranges 710 and non-invasive measurements 712 which can be utilized to perform a comprehensive heart assessment. In one instance, profile ranges 710 (e.g., baseline profile) can be established based on age, ethnicity, genetic variation/composition, and the like. Non-invasive measurements 712 can include, but is not limited to, function 714 based measurements, perfusion 716 based measurements, metabolism 718 based measurements, and the like. It shall be appreciated that one or more correlations between measurements can be established to determine variances in measurements. In one instance, profile ranges 710 can be utilized to adjust for medication and/or irregularities in health. For example, range 710 can be utilized to account for metabolism which can be slowed by medication that can also affect perfusion measurements. That is, the disclosure can utilize arbitrarily complex baseline profiles to account for wearer health idiosyncrasies.

Figure 8:
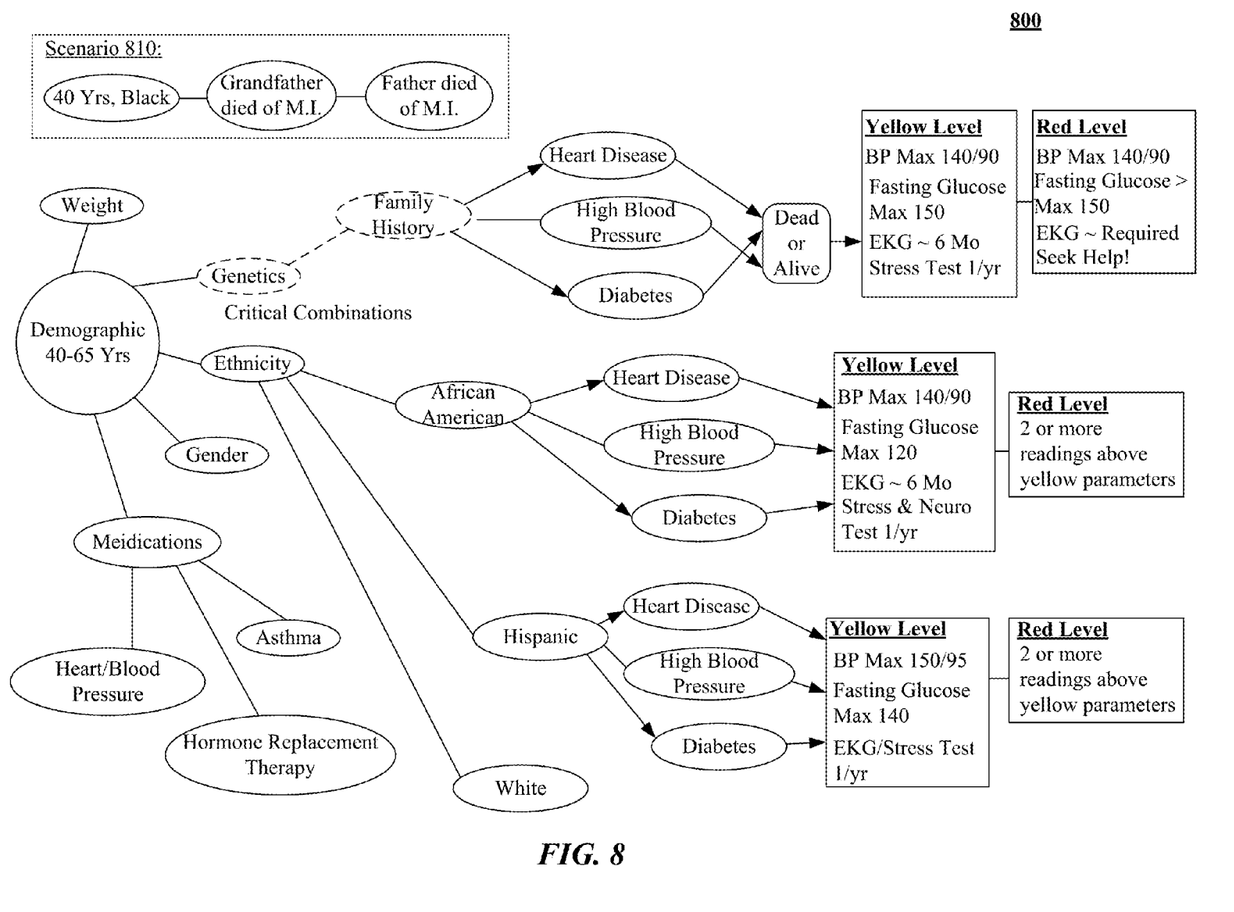
FIG. 8 is a schematic diagram illustrating a chart for enabling comprehensive heart health assessment utilizing biometrics from a wearable fitness monitor in accordance with some embodiments.

FIG. 8 is a schematic diagram illustrating a chart 800 for enabling comprehensive heart health assessment utilizing biometrics from a wearable fitness monitor in accordance with an embodiment of the inventive arrangements disclosed herein. Chart 800 can be present in the context of embodiments 110, 150, scenario 130, method 201, 251, system 300, embodiments 410, 450, 510, 530, embodiments 610, and/or chart 700.

Chart 800 illustrates a set of conditions for establishing a risk index associated with the comprehensive assessment of the disclosure. In one instance, the chart can establish a green, yellow, and red risk index level for a wearer based on assessment. In the instance, the fitness monitor can present assessment in using an LED to indicate risk. In the chart, conditions including, blood pressure maximum, resting glucose measurements can be utilized to establish a yellow level risk and/or a red level risk. For example, in scenario 810, a yellow level risk can be assessed for a 40 year old black male with a family history of death from myocardial infarction when their blood pressure is 140/90 and fasting glucose is 150. It shall be appreciated that the risk index can be arbitrarily complex.

The embodiments taught by the foregoing disclosure provide the benefit of an automated health monitoring device that adjusts its operation in order to conserve energy. By reducing the sampling rate of biometric measurements when the available energy is low, the device facilitates recharging by solar cells even when they have a low output, which prolongs the time over which a wearer can use the device, and which will therefore be more likely to sense any concerning health conditions that may arise, rather than the wearer having to remove the device so it can be recharged.

In the foregoing specification, specific embodiments have been described.

However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description as part of the original disclosure, and remain so even if cancelled from the claims during prosecution of the application, with each claim standing on its own as a separately claimed subject matter. Furthermore, subject matter not shown should not be assumed to be necessarily present, and that in some instances it may become necessary to define the claims by use of negative limitations, which are supported herein by merely not showing the subject matter disclaimed in such negative limitations.

We claim:

1. A wearable fitness monitoring device, comprising:
   at least one biometric sensor configured to sense a physiological condition of a wearer to produce a biometric parameter measurement of the physiological condition of the wearer;
   a processor coupled to the at least one biometric sensor and configured to process the biometric parameter measurement and control a sampling rate at which the biometric parameter measurement is sampled; and
   a variable energy source contained in the wearable fitness monitor that provides a variable energy level, and wherein power from the variable energy level is provided to the processor and the at least one biometric sensor;
   wherein the processor controls the sampling rate in proportion to the variable energy level of the variable energy source.

2. The wearable fitness monitoring device of claim 1, wherein the variable energy source is a battery.

3. The wearable fitness monitoring device of claim 1, wherein the variable energy source is a photovoltaic cell.

4. The wearable fitness monitoring device of claim 1, wherein the variable energy source includes a battery and a photovoltaic cell.

5. The wearable fitness monitoring device of claim 1, further comprising:
   a wrist band having an outer surface and an inner surface;
   an interior contact on the inner surface of the wrist band; and
   an exterior contact on the outer surface of the wrist band;
   wherein a biometric measurement is measured between interior contact and the exterior contact.

6. The wearable fitness monitoring device of claim 5, wherein the wrist band comprises a fastening mechanism with a friction fit clasp, wherein the clasp includes the interior and exterior contact.

7. The wearable fitness monitoring device of claim 5, wherein the device comprises of a plurality of LEDs and wherein the wearable fitness monitoring device uses the LEDS to indicate a health condition.

8. The wearable fitness monitoring device of claim 5, wherein the at least one biometric sensor, responsive to contact with the wearer's wrist at the interior contact and the wearer's thumb at the exterior contact, is configured to collect the biometric parameter associated with the wearer.

9. The wearable fitness monitoring device of claim 1, wherein the processor is configured to periodically prompt the wearer to initiate biometric collection.

10. The wearable fitness monitoring device of claim 1, wherein the wearable fitness processor is configured to determine device determines an assessment of the wearer's health based on comparing the biometric parameter measurement with a previously established baseline profile associated with the wearer.

11. A method biometric sensing for a wearable electronic health device comprising:
    collecting a plurality of biometrics by the wearable electronic health device or an interface associated with a computing device communicatively linked to the wearable electronic health device, wherein the collecting is repeated at a sampling rate;
    obtaining the plurality of biometrics from the device via at least one sensor within the device;
    monitoring a variable energy level available from a variable energy source used to power the wearable electronic health device; and
    adjusting the sampling rate based on the variable energy level, wherein the sampling rate is decreased as the variable energy level decreases.

12. The method of claim 11, wherein collecting the plurality of biometrics associated with the wearer is performed responsive to contact with a wrist of the wearer at an interior contact of the wearable electronic health device and a thumb of the wearer at an exterior contact of the wearable electronic health device.

13. The method of claim 11, further comprising periodically prompting the wearer to initiate biometric collection of a plurality of biometrics.

14. The method of claim 11, further comprising assessing a cardiac health of a wearer by comparing collected biometric with a baseline health profile of the wearer.

15. The method of claim 11, further comprising:
    recharging a rechargeable battery of the wearable electronic health device; and
    upon commencing collecting the plurality of biometrics, suspending recharging of the rechargeable battery until biometric collection is completed, and resuming recharging of the rechargeable battery upon completion of collecting the plurality of biometrics.

16. The method of claim 11, further comprising:
    analyzing the plurality of biometrics based on a previously established baseline, wherein the baseline comprises of a plurality of previously established thresholds for each of the plurality of biometrics; and
    producing an indicia which indicates the current health of a wearer based on the analyzing.

17. A wearable health monitoring device, comprising:
- a biometric sensor configured to sense a physiological condition of a wearer to produce a biometric parameter measurement of the physiological condition of the wearer;
- a processor coupled to the at least one biometric sensor and configured to control a sampling rate at which the biometric parameter measurement is sampled;
- a wireless transceiver configured to communicate the biometric parameter measurement to another device; and
- a variable energy source contained in the wearable fitness monitor that provides a variable energy level, and wherein power from the variable energy regulator is provided to the processor and the at least one biometric sensor;
- wherein the processor controls the sampling rate in proportion to the variable energy level of the variable energy source.

18. The wearable health monitoring device of claim 17, wherein the variable energy source comprises a solar cell.

19. The wearable health monitoring device of claim 17, wherein the variable energy source is a rechargeable battery.

* * * * *